United States Patent
Goodrich et al.

(10) Patent No.: US 12,065,624 B2
(45) Date of Patent: Aug. 20, 2024

(54) PHOSPHORUS REMOVAL PROCESS

(71) Applicant: Green Lizard Technologies Ltd., Belfast (GB)

(72) Inventors: Peter Goodrich, Belfast (GB); Eoghain O'Hara, Belfast (GB); Martin Atkins, Belfast (GB)

(73) Assignee: Green Lizard Technologies Ltd., Belfast (GB)

( * ) Notice: Subject to any disclaimer, the term of this patent is extended or adjusted under 35 U.S.C. 154(b) by 542 days.

(21) Appl. No.: 17/289,431

(22) PCT Filed: Oct. 29, 2019

(86) PCT No.: PCT/GB2019/053049
§ 371 (c)(1),
(2) Date: Apr. 28, 2021

(87) PCT Pub. No.: WO2020/089601
PCT Pub. Date: May 7, 2020

(65) Prior Publication Data
US 2022/0056367 A1   Feb. 24, 2022

(30) Foreign Application Priority Data
Oct. 29, 2018 (GB) .................... 1817667

(51) Int. Cl.
*C11B 3/06* (2006.01)
*A23L 5/20* (2016.01)
*C07C 215/08* (2006.01)

(52) U.S. Cl.
CPC ........... *C11B 3/06* (2013.01); *A23L 5/27* (2016.08); *C07C 215/08* (2013.01)

(58) Field of Classification Search
CPC ... C11B 3/06; C11B 3/006; A23L 5/23; C07C 215/08
See application file for complete search history.

(56) References Cited

U.S. PATENT DOCUMENTS

| | | |
|---|---|---|
| 1,885,859 A | 11/1932 | Ludwig et al. |
| 6,579,996 B2 * | 6/2003 | Peter .................... C11B 3/06 554/175 |
| 2002/0111504 A1 | 8/2002 | Peter et al. |
| 2002/0172741 A1 | 11/2002 | Thengumpillil et al. |
| 2014/0012025 A1 | 1/2014 | Sohling et al. |

FOREIGN PATENT DOCUMENTS

| | | |
|---|---|---|
| CN | 102226126 A | 10/2011 |
| GB | 391658 A | 5/1933 |

OTHER PUBLICATIONS

Oybek Zufarov et al., Ethanolamines used for degumming of rapeseed and sunflower oils as diesel fuels, European Journal of Lipid Science and Technology, vol. 111, No. 10, pp. 985-992 (Year: 2009).*
International Searchreport dated Jan. 15, 2020 for App. No. PCT/GB2019/053049.
UK Search Report for GB1817667.7 dated Apr. 30, 2019.

* cited by examiner

*Primary Examiner* — Yate' K Cutliff
(74) *Attorney, Agent, or Firm* — Ryan T. Grace; Advent, LLP

(57) ABSTRACT

The invention relates to processes for the refining of oils. In particular, the invention relates to processes for the refining of oils of biological origin such as vegetable oils.

20 Claims, No Drawings

PHOSPHORUS REMOVAL PROCESS

FIELD OF THE INVENTION

The invention relates to processes for the refining of oils. In particular, the invention relates to processes for the refining of oils of biological origin such as vegetable oils.

BACKGROUND OF THE INVENTION

Oils of biological origin such as vegetable oils and animal oils find use in many applications. Vegetable oils find use in applications such as for cooking foods and as food additives to be added to products for both human and animal consumption. Vegetable oils may also be hydrogenated or partially hydrogenated and these hydrogenated vegetable oils may also be used as food additives. Vegetable oils also find industrial uses in products such as soaps, skin products, candles, perfumes and other personal care and cosmetic products, paints, wood treatment products. Increasingly, vegetable oils are also used to produce biodiesel fuels. In this application, the triglyceride component of the vegetable oil is trans-esterified to produce mono-alkyl esters of fatty acids which form the principal component of biodiesel. The use of vegetable oils as alternative energy is growing and the availability of biodiesel around the world is increasing.

Vegetables oils may also be recycled after use. In particular, vegetable oils can be recycled from restaurants, snack food factories, potato processing plants and industrial deep fryers. The recycled oil may find use in applications such as direct fuel, conversion to biodiesel, soap, animal feed, pet food, detergent and cosmetics.

Vegetable oils are extracted from many different types of plant. Examples of plants that vegetable oils are extracted from include palm, soybean, rapeseed, sunflower seed, peanut, cottonseed, palm kernel, coconut, olive oil, safflower, canola oil and cotton seed, corn oil, groundnut, rice bran. Of these vegetables oils, palm, soybean, rapeseed and sunflower seed oil are produced globally in the highest quantities.

Vegetables oil production involves extraction of the vegetable oil from its plant components such as seeds. This is generally done via mechanical extraction which occurs in an oil mill or by using a chemical solvent. Mechanical extraction generally takes place in an oil mill and involves crushing or pressing the plant components so that they release the vegetable oil.

Methods of mechanical extraction include expeller-pressing, screw pressing, ram pressing, and using a powered pestle and mortar. Chemical solvent extraction may also be used to extract vegetable oil form plants. This typically produces higher yields and is quicker and less expensive than mechanical extraction. However, mechanical extraction is often preferred as a method of extraction over chemical extraction since it is often perceived as being a more natural and healthy way of extracting vegetable oils from plants. Many modern vegetable oil extraction methods use both mechanical and solvent extraction. A commonly used method is to use a screw to crush the raw materials in a continuous process before extraction of the oil form the press cake using a centrifuge or solvent such as hexane.

Once vegetable oils have been extracted, they often require refining before use to remove various impurities and undesirable contents. The principal component of vegetable oils are the triglyceride molecules. Impurities include organic phosphorus compounds such as phosphatides, mucilaginous materials, waxes, free fatty acids, polysaccharides and oligosaccharides, proteins, chloropropanols, glycidols, phosphorus-containing compounds and metals. Many of the phosphorus-containing compounds and metals are present because they are components of proteins which have been extracted from the plants into the vegetable oils during extraction. Glyceride oil refining processes may also extract lipids, pigments, volatile odiferous compounds and other components which either negatively impact upon the oil's stability or present potential toxicity issues.

Vegetable oil refining occurs via a variety of processes and is carried out in a vegetable oil refinery. Refining of vegetable oils is important to remove gums, waxes, phosphatides, free fatty acids (FFAs) and other impurities from the oil as well as so as to remove colouring pigments and to get rid of unpleasant smells from the oil by removing oderifous material. Typically, the first process carried out on vegetable oil in an oil refinery is a degumming process. This process typically involves hydrating the vegetable oil with water or steam, or addition of acid to the oil. This process removes organic phosphorus compounds such as phosphatides from the oil as well as other gum forming mucilaginous materials. If these materials are not removed then gum like materials may form in the vegetable oil upon storage.

After degumming, typically, deacidification processes are carried out which remove free fatty acids from the vegetable oils. If left in the vegetable oil, free fatty acids may impart a rancid or soapy flavour to the vegetable oil as well as causing other problems. Conventional processes for removing free fatty acids include treatment of the vegetable oil with aqueous alkali, by treating with steam at temperatures of around 220° C., esterification with glycerol to form triglycerides, and by using solvent extraction or absorbents. Once the free fatty acids have been removed from the vegetable oil, further processing steps include bleaching the vegetable oil, deoderisation, dewaxing, depigmentation and winterization of the vegetable oil.

A method of free fatty acid removal from vegetable oils known in the art is extraction of the free fatty acids using aqueous organic amines. An aqueous solution of an organic amine such as dimethylethanolamine is added to a vegetable oil. In this process the free fatty acids move from the triglyceride phase of the vegetable oil into the aqueous organic amine containing phase which may then be separated from the vegetable oil.

U.S. Pat. No. 6,579,996 discloses a process for removing free fatty acids from fats or oils of biological origin by extracting the free fatty acids with a mixture of basic organic nitrogen compounds and water as an extraction medium.

U.S. Pat. No. 1,885,859 discloses a process of purifying oils, fats and waxes of the ester type by contacting the material to be treated with an alkylolamine.

U.S. Pat. No. 2,164,012 discloses a process of refining fatty materials with a nitrogen-containing amine extractant, which process includes washing the raffinate obtained by the main extraction with water to remove free extractant, before washing the raffinate with dilute aqueous acid so as to remove soaps form the fatty materials.

The inventors of the present invention have appreciated that it would be useful to provide a process whereby other impurities are removed from the vegetable oil in the same process as removing free fatty acids from the vegetable oil. For example, it would be advantageous to provide a process in which phosphorus and phosphorus-containing compounds could be removed from the vegetable oil in the same process as reducing the free fatty acid content. Since phosphorus-containing compounds are generally removed from vegetable oils via degumming processes, removing the phosphorus and phosphorus-containing compounds in the same step could reduce or even eliminate the need for a degumming process to be carried out, thereby simplifying the vegetable oil refinement process.

SUMMARY OF THE INVENTION

The present invention is based on the surprising finding that organic amines can remove other impurities from glyceride oils such as vegetable oils in addition to free fatty acids. Surprisingly, it has been found that phosphorus and phosphorus-containing compounds present in glyceride oils such as vegetable oils may be removed by contacting the glyceride oil with an organic amine.

According to an aspect of the invention, there is provided the use of an organic amine for removing phosphorus and/or phosphorus containing compounds from a glyceride oil comprising phosphorus and/or phosphorus containing compounds by contacting the oil with an organic amine, wherein the organic amine is selected from:

$N(R^a)(R^b)(R^c)$, wherein: $R^a$, $R^b$, and $R^c$ are each independently selected from a $C_1$ to $C_8$, straight chain or branched alkyl group or a $C_3$ to $C_6$ cycloalkyl group; or any two of $R^a$, $R^b$ and $R^c$ combine to form an alkylene chain —(CH$_2$)$_q$— wherein q is from 3 to 6; and wherein said alkyl or cycloalkyl groups may optionally be substituted by one to three groups selected from: $C_1$ to $C_4$ alkoxy, $C_2$ to $C_8$ alkoxyalkoxy, $C_3$ to $C_6$ cycloalkyl, —OH, —NH$_2$, —SH, —CO$_2$($C_1$ to $C_6$)alkyl, and —OC(O)($C_1$ to $C_6$)alkyl; or $R^a$ is hydrogen and $R^b$, and $R^c$ are as previously defined.

According to another aspect of the invention, there is provided a process for removing phosphorus and/or phosphorus containing compounds from glyceride oil, the process comprising the steps of:

(i) contacting glyceride oil comprising phosphorus and/or phosphorus containing compounds with an organic amine and water to form a treated glyceride oil and an aqueous phase; wherein the water is added in an amount from 5% v/v to 40% v/v relative to the organic amine and the amount of organic amine is from 1 wt. % to 75 wt. % relative to the glyceride oil; wherein phosphorus is present in the glyceride oil in an amount of from 0.25 ppm to 10,000 ppm; and the organic amine is selected from:

$N(R^a)(R^b)(R^c)$, wherein: $R^a$, $R^b$, and $R^c$ are each independently selected from a $C_1$ to $C_8$, straight chain or branched alkyl group or a $C_3$ to $C_6$ cycloalkyl group; or any two of $R^a$, $R^b$ and $R^c$ combine to form an alkylene chain —(CH$_2$)$_q$— wherein q is from 3 to 6; and wherein said alkyl or cycloalkyl groups may optionally be substituted by one to three groups selected from: $C_1$ to $C_4$ alkoxy, $C_2$ to $C_8$ alkoxyalkoxy, $C_3$ to $C_6$ cycloalkyl, —OH, —NH$_2$, —SH, —CO$_2$($C_1$ to $C_6$)alkyl, and —OC(O)($C_1$ to $C_6$)alkyl; or $R^a$ is hydrogen and $R^b$, and $R^c$ are as previously defined; and (ii) separating the treated glyceride oil from the aqueous phase after contacting the glyceride oil with the organic amine and water; wherein the treated glyceride oil has a reduced concentration of phosphorus and/or phosphorus containing materials compared to the glyceride oil contacted in step (i).

DETAILED DESCRIPTION OF THE INVENTION

According to a first aspect of the invention, there is provided the use of an organic amine for removing phosphorus and/or phosphorus containing compounds from a glyceride oil comprising phosphorus and/or phosphorus containing compounds by contacting the oil with an organic amine, wherein the organic amine is selected from:

$N(R^a)(R^b)(R^c)$, wherein: $R^a$, $R^b$, and $R^c$ are each independently selected from a $C_1$ to $C_8$, straight chain or branched alkyl group or a $C_3$ to $C_6$ cycloalkyl group; or any two of $R^a$, $R^b$ and $R^c$ combine to form an alkylene chain —(CH$_2$)$_q$— wherein q is from 3 to 6; and wherein said alkyl or cycloalkyl groups may optionally be substituted by one to three groups selected from: $C_1$ to $C_4$ alkoxy, $C_2$ to $C_8$ alkoxyalkoxy, $C_3$ to $C_6$ cycloalkyl, —OH, —NH$_2$, —SH, —CO$_2$($C_1$ to $C_6$)alkyl, and —OC(O)(C) to $C_6$)alkyl; or $R^a$ is hydrogen and $R^b$, and $R^c$ are as previously defined.

The treatment of phosphorus-containing glyceride oil by contacting with an organic amine so as to reduce the phosphorus concentration may be suitably applied to crude phosphorus-containing glyceride oil which has not undergone any previous refining steps. Alternatively, the above process may be applied to phosphorus-containing glyceride oil which has undergone one or more additional refining steps prior to treatment with the organic amine.

The treatment with organic amine can therefore be integrated into a glyceride oil refining process at several stages. For instance, the treatment can be implemented at a stage at the beginning of the refining process. Alternatively, the treatment can be implemented towards the end of the refining process. This flexibility makes the treatment with organic amine in accordance with the present invention particularly attractive for integrating into pre-existing refining processes and systems.

The term "crude" used herein in reference to glyceride oil is intended to mean glyceride oil which has not undergone refining steps following oil extraction. For example, crude glyceride oil will not have undergone degumming, deacidification, winterisation, bleaching, depigmentation or deodorization. "Refined" used herein in reference to glyceride oil is intended to mean a glyceride oil which has undergone one or more refining steps, such as degumming, deacidification, winterisation, bleaching, depigmentation and/or deodorization.

Use according to the invention comprises contacting a phosphorus-containing glyceride oil with an organic amine so as to reduce the phosphorus concentration of the glyceride oil. The organic amine may be added to the glyceride oil in any suitable amount sufficient to remove phosphorus and phosphorus-containing compounds from the glyceride oil. Typically, the organic amine is added to the glyceride oil in an amount of from 1 wt. % to 80 wt. % relative to the amount of glyceride oil. Preferably, the organic amine is added in an amount of from 1 wt. % to 40 wt. % relative to the amount of glyceride oil, more preferably, from 1 wt. % to 20 wt. %, and most preferably from 2 wt. % to 8 wt. %. For example, the organic amine can be added in an amount of from 4 wt. % to 6 wt. % relative to the amount of glyceride oil, such as 5 wt. %.

Use according to the invention preferably comprises adding water to the glyceride oil as well as the organic amine. The water may be any sort of water. For example, water of varying degrees of purity may be used. More pure forms of water such as distilled water may be used, but water with various impurities present such as salts dissolved therein may also be used. The water may be present in any suitable amount sufficient for removing phosphorus and phosphorus containing compounds from the glyceride oil. For example, the water may be present in an amount of from 1% v/v to 80% v/v relative to the organic amine. Typically, the water is present in an amount of from 15% v/v to 40% v/v relative to the organic amine. Preferably, the water is present in an amount of from 25% v/v to 35% v/v, such as 30% v/v relative to the organic amine.

Alternatively, a different solvent or a mixture of solvents may be used providing the solvent(s) are compatible with the glyceride oil and organic amine. Polar solvents are preferred alternative solvents. For example, an alcohol or a mixture of water and alcohol may be used.

The organic amine used is typically a compound having the following formula:

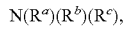

wherein: $R^a$, $R^b$, and $R^c$ are each independently selected from a $C_1$ to $C_8$, straight chain or branched alkyl group wherein said alkyl group may be unsubstituted or may be substituted by one to three groups selected from: $C_1$ to $C_4$ alkoxy, $C_2$ to $C_8$ alkoxyalkoxy, $C_3$ to $C_6$ cycloalkyl, —OH, —NH$_2$, —SH, —CO$_2$($C_1$ to $C_6$)alkyl, and —OC(O)($C_1$ to $C_6$)alkyl, for example one to three —OH or —NH$_2$ groups; or $R^a$ is hydrogen and $R^b$, and Re are as previously defined.

Preferably, the organic amine is a compound of the following formula:

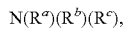

wherein: $R^a$, $R^b$, and $R^c$ are each independently selected from a $C_1$ to $C_4$, straight chain or branched alkyl group wherein at least one of $R^a$, $R^b$, and $R^c$ is substituted by a single —OH group.

More preferably, the organic amine is a tertiary amine comprising 3 alkyl chains bonded to a nitrogen atom, wherein one of the alkyl chains is substituted with an OH group.

Most preferably, the organic amine is the compound dimethylethanolamine which has the formula:

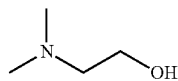

Dimethylethanolamine is highly preferred since its use as an additive in or as a reagent in the processing of food products is approved in many countries. This is particularly advantageous in applications where it is intended to use the glyceride oil in food products, or as a cooking oil.

The organic amine can be used to reduce the concentration of any form of phosphorus present in the phosphorus-containing glyceride oil. For example, the organic amine can be used to reduce the concentration of elemental phosphorus or phosphorus-containing compounds. Preferably, the phosphorus is present in the glyceride oil in the form of a phosphorus containing compound. Phosphorus containing compounds are a common component of glyceride oils such as vegetable oils because phosphorus is commonly found in many biological molecules that are found in the plants from which the vegetable oils are extracted. On extraction of the vegetable oil from plants or seeds in an oil mill, many of these biological molecules remain in the vegetable oil. Even when complex biological molecules that contain phosphorus are broken down during processing of the vegetable oil, the phosphorus may remain in the vegetable oil in one form or another such as in the form of phosphorus containing compounds.

Phosphorus containing compounds that may be present in glyceride oils and that may have their concentration in the oil reduced by use according to the invention include, but are not limited to phospholipids, phosphatides, or any combination thereof.

Phosphorus-containing compounds are desirable to remove from oil for a variety of reasons. For example, phosphorus-containing compounds such as phosphatides may contribute to the formation of gums in the vegetable oil. It is desirable to remove gums for a variety of reasons. Gums may cause high refining losses due to their emulsifying properties. Gums may also decompose, darkening the oil due to their thermal instability.

The phosphorus or phosphorus-containing compounds present in the glyceride oil are typically present in an amount of from 0.25 ppm to 50,000 ppm, and preferably from 0.25 ppm to 10,000 ppm of phosphorus before having their concentration lowered in accordance with the present invention. In some instances, phosphorus is present in the glyceride oil in an amount of from 1 ppm to 100 ppm, preferably from 10 ppm to 50 ppm, and more preferably from 10 ppm to 20 ppm.

The phosphorus content of the glyceride oil can be measured by any suitable technique known in the art. For example, the phosphorus concentration in the glyceride oil can be determined using ICP-OES analysis.

Use according to the invention comprises contacting a phosphorus-containing glyceride oil with an organic amine and preferably water. The contacting is carried out at a temperature lower than the boiling point of the organic amine. The contacting is typically carried out at a temperature of less than 130° C., or less than 80° C., preferably from 25° C. to 70° C., more preferably from 35° C. to 65° C., most preferably from 45° C. to 55° C., for example 50° C. As will be appreciated, where the glyceride oil is semi-solid at room temperature, higher temperatures are preferable such that the glyceride oil is in a liquid form for contacting with the liquid organic amine. Suitably, the contacting step is carried out at a pressure of from 0.1 MPa absolute to 10 MPa absolute (1 bar absolute to 100 bar absolute).

The contacting of phosphorus-containing glyceride oil, organic amine and preferably water typically comprises stirring the phosphorus-containing glyceride oil, organic amine and water if present for a suitable period of time. Typically, the stirring is carried out for a time period of from 1 minute to one hour, and preferably from 5 minute to 30 minutes.

The contacting is preferably carried out in a mixer such as a shear mixer. Alternatively, the contacting is carried out with an ultrasonic stirrer, an electromagnetic stirrer, or by bubbling inert gas through the mixture. Preferably, the mixture of organic amine, glyceride oil and preferably water is stirred at a speed of from 500 to 5000 rpm, preferably 3500 to 4500 rpm such as 4000 ppm.

Typically, after the step of contacting and stirring the phosphorus-containing glyceride oil, organic amine and water if present, the mixture is left so that an oil phase separates from a non-organic phase. The non-organic phase comprises the organic amine and preferably water. The oil phase comprises a treated glyceride oil with a reduced phosphorus concentration compared to the phosphorus-containing glyceride oil prior to treatment. Typically, the mixture is left for several hours to allow the two phases to separate and preferably the mixture is left over night.

Any suitable means of separating the treated glyceride oil phase and the non-organic phase may be used. For example, gravity separation (for example, in a settling unit) may be carried out. In this process, the treated glyceride oil is generally the upper phase and the organic amine and water if present form the lower phase. Separation may also be achieved using for example, a decanter, a hydrocyclone, electrostatic coalesce, a centrifuge or a membrane filter press. Contacting and separation steps may be repeated several times, for example 2 to 4 times. Preferably, separation is carried out via centrifugation.

Contacting and separation steps may also be carried out together in a counter-current reaction column. The glyceride oil (hereinafter "oil feed stream") is generally introduced at or near the bottom of the counter-current reaction column and the organic amine (hereinafter "organic amine feed stream") at or near the top of the counter-current reaction column. A treated oil phase (hereinafter "product oil stream") is withdrawn from the top of the column and a phase containing an organic amine and solvent when present (hereinafter "secondary stream") from at or near the bottom thereof. Preferably, the counter-current reaction column has a sump region for collecting the secondary stream. Preferably, the oil feed stream is introduced to the counter-current reaction column immediately above the sump region. More than one counter-current reaction column may be employed, for example 2 to 6, preferably 2 to 3 columns arranged in series. Preferably, the counter-current reaction column is packed with a structured packing material, for example, glass Raschig rings, thereby increasing the flow path for the oil and organic amine through the column. Alternatively, the counter-current reaction column may contain a plurality of trays.

In some instances, contacting and separating steps are carried out together in a centrifugal contact separator, for example, a centrifugal contact separator as described in U.S. Pat. Nos. 4,959,158, 5,571,070, 5,591,340, 5,762,800, WO 99/12650, and WO 00/29120. Suitable centrifugal contact separators include those supplied by Costner Industries Nevada, Inc. Glyceride oil and the organic amine may be introduced into an annular mixing zone of the centrifugal contact separator. Preferably, the glyceride oil and the organic amine are introduced as separate feed streams into the annular mixing zone. The glyceride oil and the organic amine are rapidly mixed in the annular mixing zone. The resulting mixture is then passed to a separation zone wherein a centrifugal force is applied to the mixture to produce a clean separation of an oil phase and a secondary phase.

Preferably, a plurality of centrifugal contact separators are used in series, preferably, 2 to 6, for example 2 to 3. Preferably, the oil feed stream is introduced into the first centrifugal contact separator in the series while the organic amine feed stream is introduced into the last centrifugal contact separator in the series such that oil of progressively decreasing content of, for instance, free fatty acid (FFA), phosphorus or phosphorus-containing compounds is passed from the first through to the last centrifugal contact separator in the series while an organic amine stream of progressively increasing content of, for instance, FFA, phosphorus or phosphorus-containing compounds content is passed from the last through to the first centrifugal contact separator in the series. Thus, a phase containing an organic amine, phosphorus, phosphorus-containing compounds and FFA is removed from the first centrifugal contact separator and the treated oil phase is removed from the last centrifugal contact separator in the series.

The treated glyceride oil may also be passed through a coalescer filter for coalescing fine droplets of non-oil phase liquid, so as to produce a continuous phase and facilitate phase separation. Preferably, where the organic amine used for contact is used in combination with a solvent, the coalescer filter is wetted with the same solvent to improve filtration.

After the organic amine, glyceride oil and preferably water have been contacted and separated, a treated glyceride oil is separated from a non-organic phase. The treated glyceride oil has a lower phosphorus concentration than before it was contacted with the organic amine. Typically, the treated glyceride oil has a phosphorus concentration which is less than 90% of the phosphorus-containing glyceride oil before treatment. For example, the treated glyceride oil may have a phosphorus content which is less than 80%, 70%, 60%, 50%, 40%, 30%, 20%, or 10% of the concentration of the phosphorus-containing glyceride oil before treatment.

Preferably, the treated glyceride oil has a phosphorus concentration of less than 10% and most preferably less than 5% of the phosphorus-containing glyceride oil before treatment.

The treated glyceride oil may be further treated so as to remove residual organic amine that may be present in the treated glyceride oil. For example, the treated glyceride oil may be washed with a small quantity of water (for example 100 ml) so as to reduce the concentration of any residual organic amine present in the treated glyceride oil.

The treated glyceride oil may then be dried to further reduce the concentration of residual organic amine present in the treated glyceride oil. For example, organic amine may be removed from the treated glyceride oil by vacuum drying. Alternatively, organic amine may be removed from the treated glyceride oil by vacuum distillation.

Use according to the invention may comprise contacting organic amine and any type of phosphorus-containing glyceride oil. The phosphorus-containing glyceride oil may comprise an animal oil or a vegetable oil. Preferably, the phosphorus-containing oil comprises a vegetable oil.

The term "glyceride oil" used herein refers to an oil or fat which comprises triglycerides as the major component thereof. For example, the triglyceride component may be at least 50 wt. % of the glyceride oil. The glyceride oil may also include mono- and/or di-glycerides. Preferably, the glyceride oil is at least partially obtained from a natural source (for example, a plant, animal or fish/crustacean source) and is also preferably edible. Glyceride oils include vegetable oils, marine oils and animal oils/fats which typically also include phospholipid components in their crude form. Typically, the phosphorus-containing glyceride oil comprises a vegetable oil or animal oil that is liquid at room temperature. However, the phosphorus-containing glyceride oil may comprise a vegetable oil or animal oil that is solid at room temperature. In this scenario, the contacting of the glyceride oil with the organic amine may be done at a temperature above room temperature and above the melting point of the glyceride oil.

Vegetable oils include all plant, nut and seed oils. Examples of suitable vegetable oils which may be of use in the present invention include: açai oil, almond oil, beech oil, cashew oil, coconut oil, colza oil, corn oil, cottonseed oil, grapefruit seed oil, grape seed oil, groundnut oil, hazelnut oil, hemp oil, lemon oil, macadamia oil, mustard oil, olive oil, orange oil, palm oil, palm kernel oil, peanut oil, pecan oil, pine nut oil, pistachio oil, poppyseed oil, rapeseed oil, rice bran oil, safflower oil, sesame oil, soybean oil, sunflower oil, walnut oil and wheat germ oil.

Suitable marine oils include oils derived from the tissues of oily fish or crustaceans (e.g. krill). Examples of suitable animal oils/fats include pig fat (lard), duck fat, goose fat, tallow oil, and butter.

Preferably, the phosphorus-containing glyceride oil comprises vegetable oil. Preferred vegetable oils include coconut oil, corn oil, cottonseed oil, groundnut oil, olive oil, palm oil, rapeseed oil, rice bran oil, safflower oil, soybean oil, sunflower oil, or mixtures thereof.

The term "soybean oil" used herein includes oil extracted from the seeds of the soybean (*Glycine max*). The term "rapeseed oil" used herein is synonymous with canola oil and refers to the oil derived from a species of rape plant, for example rapeseed (*Brassica napus* L.) or field mustard/turnip rape (*Brassica rapa* subsp. *oleifera*, syn. *B. campestris* L.). The term "palm oil" used herein includes an oil at least partially derived from a tree of genus *Elaeis*, forming part of the Arecaceae genera, and including the species *Elaeis guineensis* (African oil palm) and *Elaeis oleifera* (American oil palm), or hybrids thereof. Reference to palm oil herein therefore also includes palm kernel oil, as well as fractionated palm oil, for example palm oil stearin or palm oil olein fractions.

In instances of the present disclosure, the phosphorus-containing glyceride oil comprises a cooking oil, such as a vegetable cooking oil. In some instances, the phosphorus-containing glyceride oil comprises a used oil. In some instances, the phosphorus-containing glyceride oil comprises a used vegetable oil, and preferably a used vegetable cooking oil.

Use according to the invention may also comprise reducing the free fatty acid (FFA) content of the phosphorus-containing glyceride oil. Glyceride oils often comprise free fatty acid molecules which it is desirable to remove from the glyceride oil during its refinement. FFA which may be present in the glyceride oils include monounsaturated, polyunsaturated and saturated FFA. Examples of unsaturated FFA include: myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid and docosahexaenoic acid. Examples of saturated FFA include: caprylic acid, capric acid, undecylic acid, lauric acid, tridecylic acid, myristic acid, palmitic acid, margaric acid, stearic acid, nonadecylic acid, arachidic acid, heneicosylic acid, behenic acid, lignoceric acid and cerotic acid.

In instances of the invention, the free fatty acids are present in the phosphorus-containing glyceride oil in an amount of from 1 wt. % to 50 wt. %, preferably 1 wt. % to 30 wt. %, more preferably 5 wt. % to 25 wt. %, and most preferably 5 wt. % to 20 wt. %.

After treatment with organic amine in accordance with use according to the invention, the free fatty acid content of the glyceride oil is typically reduced to from 0.1 wt. % to 10 wt. %, preferably, 0.1 wt. % to 5 wt. %, more preferably 0.1 wt. % to 1 wt. %, and most preferably 0.25 wt. % to 1 wt. %.

Fatty acid content in the glyceride oil may be determined using standard test procedures in the art such as ASTM D5555.

Use according to the invention may comprise subjecting the treated glyceride oil to further treatment. Further treatment is typically done to the treated glyceride oil as part of a typical glyceride oil refinement process.

The skilled person is aware of the different refining steps typically used in edible oil processing, including for example refining steps discussed in: "Practical Guide to Vegetable Oil Processing", 2008, Monoj K. Gupta, AOCS Press, as well as in the Edible Oil Processing section of the "AOCS Lipid Library" website (lipidlibrary.aocs.org).

The further treatment may comprise one or more steps selected from degumming, bleaching, winterisation, depigmentation, and deoderisation. Preferably, the further treatment comprises deoderisation and/or bleaching.

In some instances, the at least one further treating step comprises the steps of degumming, bleaching and deodorization. Alternatively, in other instances, the at least one further treating step comprises a deodorisation step and the process does not comprise a step of degumming and/or bleaching. Therefore, in exemplary instances, the at least one further treating step comprises the steps of degumming and deodorization, but no bleaching. In other exemplary instances, the at least one further refining step comprises the steps of bleaching and deodorization, but no degumming step.

An additional advantage of the treatment with organic amine in accordance with the present invention is that the treatment has also been found to at least partially remove pigments and odiferous compounds which are typically removed in a high temperature (for example, 240° C. to 270° C.) deodorization step during conventional refining processes. Treatment of glyceride oil with the organic amine means that lower temperatures and/or time periods can be used for the deodorization step as part of the overall refining process. This has the advantage of reducing the energy requirements of the refining process.

Degumming typically involves contacting the oil with aqueous phosphoric acid and/or aqueous citric acid to remove both hydratable and non-hydratable phosphatides (NHP). Typically, citric acid or phosphoric acid is added as a 50 wt % aqueous solution. Suitably, the aqueous acid is used in an amount of about 0.02% to about 0.20% of acid by weight of oil, preferably 0.05% to about 0.10% of acid by weight of oil. Suitably, the degumming step is carried out at a temperature of from about 50 to 110° C., preferably 80° C. to 100° C., for example 90° C. The degumming step may suitably last from 5 minutes to 60 minutes, preferably 15 to 45 minutes, more preferably, 20 to 40 minutes, for example 30 minutes. After settling of the mucilage following the acid treatment, the aqueous phase is separated before the degummed oil is typically dried. Drying of the degummed oil suitably takes place at a temperature of from 80 to 110° C. for a suitable time period, for example 20 to 40 min, at reduced pressure, for instance, at 2 to 3 kPa (20 to 30 mbar).

As the skilled person is aware, for glyceride oils with low phosphatide content (for example, less than 20 ppm by weight of phosphorus), a dry degumming process may be used in which the phosphoric acid or citric acid is added without significant dilution with water (for example, an 85% acid solution). NHP are converted into phosphatidic acid and a calcium or magnesium bi-phosphate salt which can be removed from the oil in a subsequent bleaching step. For oils rich in phosphatides, particularly NHP, dry degumming is known to be less well suited since excessive amounts of bleaching earth are required.

Bleaching is incorporated into an edible oil refining process to reduce colour bodies, including chlorophyll, residual soap and gums, trace metals and oxidation products. Bleaching typically involves contacting the oil with an amount of bleaching clay or earth, for example from 0.5 to 5 wt. % clay based on the mass of the oil. Bleaching clays or earths are typically composed of one or more of three types of clay minerals: calcium montmorillonite, attapulgite, and sepiolite. Any suitable bleaching clay or earth may be used in accordance with the present invention, including neutral and acid activated clays (e.g. bentonite). The oil is suitably contacted with bleaching clay for 15 to 45 minutes, preferably 20 to 40 minutes before the earth is separated, typically be filtration. The oil is typically contacted with bleaching clay or earth at a temperature of from 80° C.to 125° C., preferably at a temperature of from 90° C. to 110° C. Following an initial period of contact ("wet bleaching") conducted under atmospheric pressure, a second stage of the bleaching process is conducted under reduced pressure ("dry bleaching"), for example at 2 to 3 kPa (20 to 30 mbar).

Conventional glyceride oil refining processes typically include a FFA neutralisation step with a strong base, for example sodium hydroxide or potassium hydroxide (corresponding to a so called "chemical refining" process). Alternatively, deacidification can be achieved by adjusting the deodorisation parameters accordingly to ensure that volatile FFA is removed in that step (a so called "physical refining" process). A disadvantage of a FFA neutralisation step ("chemical refining") is that it is accompanied by unwanted saponification, lowering triglyceride content, whilst soap formation can lead to substantial neutral oil losses as a result of emulsification. The organic amine treatment forming part of the use of the present invention is effective at neutralising FFA in the oil and may entirely replace a conventional neutralisation step used in a chemical refining process. Advantageously, treatment with the organic amine has the benefit that it does not lead to saponification of neutral oil. Thus, in preferred instances of the present invention, the refining process does not include a neutralisation step with an inorganic base (e.g. sodium hydroxide).

FFA present in the oil may be neutralised upon contact with the organic amine to form a salt. In preferred instances, the amount of organic amine employed in the contacting step is at least stoichiometric with the molar amount of FFA contained in the oil. For example, the molar ratio of the organic amine to FFA in the oil may be from 1:1 to 10:1, or from 1.5:1 to 5:1. The content of FFA in the glyceride oil may be determined prior to treatment with organic amine using common titration techniques, of which the person of skill in the art is aware. For instance, titration with sodium hydroxide using phenolphthalein indicator may be used to determine the FFA content of glyceride oil.

As the skilled person is aware, deodorization corresponds to a stripping process in which an amount of stripping agent is passed through an oil in a distillation apparatus, typically by means of direct injection, at reduced pressure for a period of time so as to vaporize and extract volatile components, such as FFA, aldehydes, ketones, alcohols, hydrocarbons, tocopherols, sterols, and phytosterols. The stripping agent is preferably steam, although other agents such as nitrogen may be used. The amount of stripping agent suitably used is from about 0.5% to about 5% by weight of oil.

The temperature range of deodorization for the refining process according to the present invention is suitably from 160° C.to 270° C. Where reference is made herein to the temperature of the deodorization step, this refers to the temperature the oil is heated to before being exposed to the stripping agent. The pressure range of deodorization is suitably from 0.1 to 0.4 kPa (1 to 4 mbar), preferably 0.2-0.3 kPa (2 to 3 mbar). Suitable time periods for deodorization are typically from 30 to 180 minutes, for example 60 to 120 minutes, or 60 to 90 minutes.

The skilled person is able to determine a suitable length of deodorization by analysing the appearance and composition of the glyceride oil. For instance, determining the p-anisidine value (AnV) of the oil. The p-anisidine value of an oil is a measure of its oxidative state and, more specifically, provides information regarding the level of secondary oxidation products contained in an oil, although primarily aldehydes such as 2-alkenals and 2,4-dienals. The p-anisidine value (AnV) therefore also gives an indication of the level of oxidation products which are intended to be removed by means of the deodorization step. For instance, satisfactory deodorization may be achieved where, for example, the AnV is less than 10, preferably less than 5, as determined by AOCS Official Method Cd 18-90.

In addition or alternatively, the amount of aldehyde and ketone components of the oil can be determined, which are typically associated with a crude oil's odour, to determine whether sufficient deodorization has taken place. Typical volatile odiferous aldehyde and ketone components of crude or rancid palm oil include: acetaldehyde, benzaldehyde, n-propanal, n-butanal, n-pentanal, n-hexanal, n-octanal, n-nonanal, 2-butenal, 3-methylbutanal, 2-methylbutanal, 2-pentenal, 2-hexenal, 2E,4E-decadienal, 2E,4Z-decadienal, 2-butanone, 2-pentanone, 4-methyl-2-pentanone, 2-heptanone, 2-nonanone. Preferably, each of these components is individually present in a deodorized oil in an amount less than 3 mg/kg of oil, more preferably less than 1 mg/kg of oil, most preferably less than 0.5 mg/kg of oil.

The amount of aldehydes and ketones may be readily determined by chromatographic methods, for instance GC-TOFMS or GCxGC-TOFMS. Alternatively, derivatization of aldehydes and ketones may be used to improve chromatographic analysis. For example, it is known that aldehydes and ketones may be derivatized with 2.4-dinitrophenylhydrazine (DNPH) under acidic conditions. This reagent does not react with carboxylic acids or esters and therefore the analysis is not affected by the presence of such components in a glyceride oil sample. Following derivatization, HPLC-UV analysis can quantify the total amount of aldehydes and ketones which are present in a sample.

Conventional deodorisation temperatures are typically in excess of 220° C., for example 240° C. to 270° C., and typically operated for 60 to 90 minutes. Where lower than conventional temperatures are used for deodorisation as allowed by the process of the present invention, for example 160° C.to 200° C., the time periods for deodorization may be lengthened to ensure sufficient deodorization, yet still involve less energy consumption than a conventional deodorization operated at higher temperature, for example 240° C.to 270° C., for a shorter period.

In preferred instances, the same or lower than conventional deodorization time periods are used in combination with the lower than conventional deodorization temperature, yet achieve the same extent of deodorization as a result of the preceding organic amine treatment. In other preferred instances, where conventional temperatures are used for the deodorization step included in the refining process of the invention, for example 240° C.to 270° C., the time period for the deodorization may be reduced compared to that which is conventionally used and still achieve a comparable level of deodorization as a result of the preceding organic amine treatment.

In particularly preferred instances, where the at least one further refining step according to use of the present invention comprises deodorisation, the temperature of the deodorization is from 160° C. to 200° C., more preferably 170° C. to 190° C. Preferably, the time periods over which deodorization is conducted at these temperatures is from 30 to 150 minutes, more preferably 45 to 120 minutes, most preferably 60 to 90 minutes.

The organic amine treatment according to the use of the present invention may suitably be applied to crude metal-containing glyceride oil which has not undergone any previous refining steps following oil extraction. Alternatively, use of the present invention may be applied to glyceride oil which has undergone at least one additional refining step prior to treatment organic amine. Typically, the at least one additional refining step is selected from bleaching and/or degumming.

An advantage associated with use according to the invention is that the degumming requirement of the glyceride oil is reduced or eliminated. Phosphorus-containing compounds such as phosphatides are partly responsible for formation of gums in glyceride oils and they are conventionally removed in conventional degumming processes. Since use according to the invention reduces the concentration of phosphorus and phosphor-containing compounds in the glyceride oil, the requirement to degum the glyceride oils may be eliminated or reduced. In instances where a degumming process is performed on the glyceride oil after the organic amine treatment in accordance with use according to the invention, less acid may be required in said degumming step since many phosphorus-containing compounds will have been removed in accordance with use according to the invention.

In instances, the glyceride oil has not been degummed before treatment with organic amine in accordance with use according to the invention. In such instances, use according to the invention may comprise not subjecting the glyceride oil to further treatment. Alternatively, where the glyceride has not been degummed before treatment with organic amine in accordance with use according to the invention, and where use according to the invention comprises subjecting the glyceride oil to further treatment, the further treatment may not comprise a degumming process. Accordingly, in some instances, use according to the invention may eliminate the requirement for a carrying out a degumming process in refining the glyceride oil.

According to a second aspect of the invention, there is provided a process for removing phosphorus and/or phosphorus-containing compounds from glyceride oil, the process comprising the steps of:

(i) contacting glyceride oil comprising phosphorus and/or phosphorus-containing compounds with an organic amine and water to form a treated glyceride oil and an aqueous phase; wherein the water is added in an amount from 5% v/v to 40% v/v relative to the organic amine and the amount of organic amine is from 1 wt. % to 75 wt. % relative to the glyceride oil; wherein phosphorous is present in the glyceride oil in an amount of from 0.25 ppm to 10,000 ppm; and the organic amine is selected from:

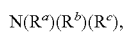

$N(R^a)(R^b)(R^c)$, wherein: $R^a$, $R^b$, and $R^c$ are each independently selected from a $C_1$ to $C_8$, straight chain or branched alkyl group or a $C_3$ to $C_6$ cycloalkyl group; or any two of $R^a$, $R^b$ and $R^c$ combine to form an alkylene chain $—(CH_2)_q—$ wherein q is from 3 to 6; and wherein said alkyl or cycloalkyl groups may optionally be substituted by one to three groups selected from: $C_1$ to $C_4$ alkoxy, $C_2$ to $C_8$ alkoxyalkoxy, $C_3$ to $C_6$ cycloalkyl, $—OH$, $—NH_2$, $—SH$, $—CO_2(C_1$ to $C_6)$alkyl, and $—OC(O)(C_1$ to $C_6)$alkyl; or $R^a$ is hydrogen and $R^b$, and $R^c$ are as previously defined; and (ii) separating the treated glyceride oil from the aqueous phase after contacting the glyceride oil with the organic amine and water; wherein the treated glyceride oil has a reduced concentration of phosphorous and/or phosphorous containing materials compared to the glyceride oil contacted in step (i).

Preferably, the phosphorus-containing glyceride oil has a phosphorous content of from 1 ppm to 100 ppm, more preferably from 10 ppm to 50 ppm, and most preferably from 10 ppm to 20 ppm.

In some instances, the process of the invention is a pre-treatment process. The term "pre-treatment process" as used herein is used to refer to a treatment carried out to the phosphorus-containing glyceride oil before any other refining step (such as the steps discussed above). Thus, in instances, the pre-treatment process is carried out directly after extraction of the phosphorus-containing glyceride oil and prior to any other step of processing the phosphorus-containing glyceride oil.

Alternatively, in instances where the phosphorus-containing glyceride oil comprises a used oil, the term "pre-treatment process" refers to where the pre-treatment process is carried out prior to any other processing step of the used oil, and after collection of the used oil.

Preferably, the process eliminates or reduces the need to subsequently degum the glyceride oil. In some instances, where the glyceride oil has not been degummed beforehand, the process does not comprise further treatment; or the process comprises further treatment, wherein the further treatment does not comprise a degumming process.

Any of the features and preferred features discussed above in relation to the first aspect of the invention equally apply to this aspect of the invention. In particular, all features of the organic amine, phosphorus-containing glyceride oil, phosphorus and phosphorus-containing compounds, contacting and separation steps, and further treatments discussed above in relation to the first aspect of the invention apply equally to the process according to the second aspect of the invention.

Use according to the first aspect of the invention, and processes according to the second aspect of the invention may further comprise the step of regenerating the organic amine from the aqueous phase. Preferably, the step of regenerating the organic amine from the aqueous phase comprises vacuum distillation.

Instances of the invention described hereinbefore may be combined with any other compatible instances to form further instances of the invention.

The present invention will now be illustrated by way of the following examples.

EXAMPLES

Crude palm oil (CPO) (130 g, 5.25%, 0.0269 mol FFA) was heated to 50° C. The liquid was stirred with a high shear mixer at 4000 rpm. Aqueous dimethylethanolamine (70% v/v) (DMEA) (2.519 g, 0.0282 mol) was added. The solution was stirred for 15 minutes before centrifugation. An oil phase was separated from a non-organic phase.

FFA levels in the separated oil phase were determined by colorimetric titration. Typically, 1 g of oil was dissolved in 25 ml isopropyl alcohol (IPA), before a few drops of phenolphthalein were added and the solution was titrated against 0.1M potassium hydroxide solution. The initial FFA value of 5.25% in the crude palm oil was reduced to 0.3% after treatment with DMEA.

Phosphorus concentration was calculated in both the crude palm oil (CPO) and in the separated treated palm oil (TPO) using ICP-OES analysis.

|  | CPO Test 1 | CPO Test 2 | TPO Test 1 | TPO Test 2 |
| --- | --- | --- | --- | --- |
| Phosphorus content (ppm) | 14.6 | 18.6 | 0.32 | 0.41 |

The above examples demonstrate that organic amines can reduce the phosphorus content of phosphorus-containing glyceride oils. The examples also demonstrate that the organic amines reduce the free fatty acid concentration of the metal-containing glyceride oils. The allowable limit of phosphorus in Refined Bleached Deodorised Palm Oil (RBDPO) is 5 ppm. Accordingly, the examples demonstrate that organic amine treatment can reduce the phosphorus content of crude vegetable oil to be within the specification of RBDPO.

The invention claimed is:

1. A process for removing phosphorus and/or phosphorus-containing compounds from glyceride oil, the process comprising the steps of:
   (i) contacting glyceride oil comprising phosphorus and/or phosphorus-containing compounds with an organic amine and water to form a treated glyceride oil and an aqueous phase; wherein the water is added in an amount from 5% v/v to 40% v/v relative to the organic amine and the amount of organic amine is from 1 wt. % to 75 wt. % relative to the glyceride oil; wherein phosphorus is present in the glyceride oil in an amount of from 0.25 ppm to 10,000 ppm, and the organic amine is dimethylethanolamine:

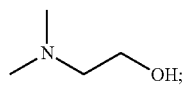

and
   (ii) separating the treated glyceride oil from the aqueous phase after contacting the glyceride oil with the organic amine and water; wherein the treated glyceride oil has a reduced concentration of phosphorus and/or phosphorus-containing materials compared to the glyceride oil contacted in step (i).

2. The process according to claim 1, wherein the glyceride oil has a phosphorus content of from 1 ppm to 100 ppm.

3. The process according to claim 1, wherein the water is added in an amount from 15% v/v to 40% v/v relative to the organic amine.

4. The process according to claim 1, wherein the amount of organic amine used is from 1 wt. % to 40 wt. % relative to the glyceride oil.

5. The process according to claim 1, wherein the organic amine is contacted with the glyceride oil at a temperature from 25 to 70° C.

6. The process according to claim 1, wherein contacting the glyceride oil with the organic amine comprises stirring a mixture of the organic amine and metal-containing glyceride oil.

7. The process according to claim 6, wherein the mixture is stirred for a time period of from 5 to 30 minutes.

8. The process according to claim 1, wherein the phosphorus and/or phosphorus-containing compounds comprise phospholipids, phosphatides, or combinations thereof.

9. The process according to claim 1, wherein the glyceride oil is a vegetable oil.

10. The process according to claim 1, wherein the glyceride oil comprises a used vegetable cooking oil.

11. The process according to claim 1, wherein the treated glyceride oil which is separated has a total concentration of phosphorus which is less than 50 wt. % than that of the glyceride oil which is contacted with the organic amine.

12. The process according to claim 1, wherein residual organic amine is removed from the treated glyceride oil.

13. The process according to claim 12, wherein the residual organic amine is removed from the glyceride oil at least in part by vacuum distillation, or vacuum drying.

14. The process according to claim 13, wherein the vacuum distillation is conducted at a temperature of from 25 to 70° C.

15. The process according to claim 1, wherein the treated glyceride oil undergoes further treatment.

16. The process according to claim 15, wherein the further treatment comprises one or more steps selected from degumming, bleaching, winterization, depigmentation and deodorization.

17. The process according to claim 16, wherein the further treatment comprises deodorization and bleaching.

18. The process according to claim 1, wherein the process eliminates or reduces the need to subsequently degum the glyceride oil.

19. The process according to claim 1, wherein the glyceride oil has not been degummed beforehand, and wherein (i) the process does not comprise further treatment, or (ii) the process comprises further treatment, wherein the further treatment does not comprise a degumming process.

20. The process according to claim 1, further comprising the step of regenerating the organic amine from the aqueous phase.

* * * * *